United States Patent [19]

Lee et al.

[11] Patent Number: 5,550,028
[45] Date of Patent: Aug. 27, 1996

[54] TETRAHYDROXYQUINONE AS AN ACTIVATOR COMPONENT FOR ACTIVATED PARTIAL THROMBOPLASTIN TIME TEST OF BLOOD COAGULATION

[75] Inventors: Ted C. K. Lee, Plantation; Franz H. Pelzer; Leslie A. Motley, both of Miami, all of Fla.

[73] Assignee: Dade International Inc., Deerfield, Ill.

[21] Appl. No.: 484,373

[22] Filed: Jun. 7, 1995

Related U.S. Application Data

[63] Continuation of Ser. No. 148,139, Nov. 4, 1993, abandoned.

[51] Int. Cl.$^6$ .............................. C12Q 1/56; C12Q 1/00; G01N 33/86; A01N 55/02
[52] U.S. Cl. ................... 435/13; 435/4; 436/74; 436/69; 436/63; 436/34; 436/16; 514/187; 514/834
[58] Field of Search ................... 435/13, 4, 7.91; 436/63, 74, 69, 34, 16; 514/187, 834

[56] References Cited

U.S. PATENT DOCUMENTS

| | | | |
|---|---|---|---|
| 3,486,981 | 12/1969 | Speck | 195/99 |
| 3,764,700 | 10/1973 | Esteve-Subirana | 514/576 |
| 3,839,317 | 10/1974 | Higuchi | 536/6.1 |
| 3,880,714 | 4/1975 | Babson | 195/99 |
| 4,672,030 | 6/1987 | Witt | 435/13 |
| 5,126,247 | 6/1992 | Palmer et al. | 435/25 |
| 5,210,239 | 5/1993 | Abe et al. | 548/195 |
| 5,302,531 | 4/1994 | Baver | 436/74 |
| 5,413,786 | 5/1995 | Anraku | 435/13 |

FOREIGN PATENT DOCUMENTS

| | | |
|---|---|---|
| WO90/11368 | 10/1990 | WIPO . |
| WO91/16453 | 10/1991 | WIPO . |

OTHER PUBLICATIONS

Biochemistry, vol. 20, No. 25, Dec. 8, 1981, Easton, PA, pp. 7258–7266, Bock et al., 'Activation of Intrinsic Blood Coagulation by Ellagic Acid . . . '.
Olah et al; Chem Abstracts, vol. 119:225500p (1993).
Derwent database abstract, JP A 60174952, Sekisui Chem. Ind. K.K., Sep. 9, 1985.
Blood coagulaton accelertor contg. non–enzymatic activator and hydrolase for bond between opt. amino acid radical and arginine or lysine radical, Derwent abstract of Japense doc. JP60174952 (1985), Sikisui Chem Ind. KK.
P. Meier and P. Gygax, *Thrombosis Research* 59; 883–886 (1990), A Comparison of Different Reagents for the Activated Partial Thromboplastin Time in Rabbit and Rat Plasma
Feiser and Fieser, Organic Chemistry, 3rd Ed. (1956) p. 716.
Willstatter and Pfannenstiel, Ueber–O –Chinon, Chem. Ber. 37, 4744–4746 (1904).
Agent accelerating blood coagulation–containing cyclic organic compound with vicinyl carbonyl groups amine salt, anti–fibrinolytic and/or anti–plasmin agent and hydrolase, Derwent abstract of Japanse doc. JP 63275524 (1988), Sekisui Chem Ind KK.
Blood coagulation accelerator comprising cyclic organic compound containing two adjacent ring–ketone groups, Derwent abstract of Japanse doc. JP 60115519 (1985), Sekisui Chem Ind KK.
Benzoquinoline derivativies preparation by cyclising 1,2,3, 4, tetrahydro–2–oxoquinoline derivatives, Derwent abstract of Japanese doc. JP 57082371 (1982), Yoshitomi Pharm Ind. KK.
Plasminogen activator preparation by contacting normal human diploid cell with peptone, quinone and thrombin, Derwent abstract of Japanse doc. JP 62026231 (1987), Asahi Chemical Ind. KK.
2–hydroxy–3–methyl–1, 4–napthoquinine prepn – for use as blood coagulant by reacting . . . Derwent abstract of Japanese doc JP 53015353, (1978), Kawasaki Chem Ind KK.

*Primary Examiner*—John Kight
*Assistant Examiner*—Louise N. Leary
*Attorney, Agent, or Firm*—Lois K. Winston; Cynthia G. Tymeson

[57] ABSTRACT

The compound 2,3,5,6-tetrahydroxy-1,4-quinone, its derivatives and structural analogs are used as activators for intrinsic blood coagulation and as diagnostic reagents for the activated partial thromboplastin time test of blood coagulation.

15 Claims, No Drawings

TETRAHYDROXYQUINONE AS AN ACTIVATOR COMPONENT FOR ACTIVATED PARTIAL THROMBOPLASTIN TIME TEST OF BLOOD COAGULATION

This is a continuation of application Ser. No. 08/148,139 filed on Nov. 4, 1993, now abandoned.

BACKGROUND OF THE INVENTION

1. Field of the Invention

This invention relates to the use of 2,3,5,6-tetrahydroxy-1,4-quinone and related compounds as an activator for intrinsic blood coagulation and for use as a diagnostic reagent for the activated partial thromboplastin time test of blood coagulation.

2. Description of Related Art

The activated partial thromboplastin time (APTT) test measures the clotting time required for blood coagulation of the intrinsic blood coagulation pathway. The blood coagulation mechanism is a complex series of interrelated protein reactions which may be thought of as occurring in a "cascade" effect. The last stares of the cascade involve the formation of a visible blood clot (whole blood trapped in a mesh of fibrin strands). The intrinsic system's pathway utilizes constituents which are present in the blood plasma. As is known to those skilled in the art, the clotting of plasma in vertebrate blood centers around the fibrinogen molecule, a large protein (MW 340,000 in the human species) with a disulfide bridged doublet structure three different constituent chains: $(\alpha\beta B)_2$. Another substrate known as "cold insoluble globulin" (MW 400,000) may also be involved by helping to anchor the fibrin network to the surface of fibroblasts. The clotting of fibrinogen is controlled in a consecutive manner by two different enzymes, thrombin (factor $II_a$, a serine protease) and fibrin stabilizing factor, a transamidase with a cysteine-SH active center (factor $XIII_a$). In the intrinsic pathway, the chain of events leading to coagulation is triggered by the exposure of plasma to nonendothelial surfaces such as glass in vitro.

The protein components of the pathway include zymogens (Factors XII, XI, IX, X, II and XIII) and regulatory proteins concerned with activation (Factors VIII and V) or inhibition processes ("antithrombin III")). In general, the regulatory proteins of activation require the participation of phospholipids (e.g. cephalin, phosphatidylethanolamine, lecithin) and of calcium ($Ca^{2+}$) ions.

The first phase in the intrinsic mechanism is the activation of Factor XII. The major function of the activated Factor XII, Factor $XII_a$, is the activation of the plasma thromboplastin antecedent (PTA, Factor XI) which, with the presence of ionic calcium, activates another coagulation component (Factor IX). The combination of activated Factor IX, Factor $VIII_a$ and of platelet factor 3 (a phospholipid), forms an agent which activates the Stuart-Prower factor (SPF, Factor X). The activated SPF in the presence of the labile factor (Factor V) form a complex which catalyzes the conversation of prothrombin (Factor II) to thrombin in the presence of ionic calcium.

Thus, after the initial interaction of tissue, platelet and plasma factors, prothrombin is activated to thrombin, a hydrolytic enzyme of great specificity. Thrombin (Factor $II_a$) brings about the conversion of fibrinogen to fibrin and it also regulates the rate of formation of fibrin stabilizing factor (Factor $XIII_a$), a transaminating enzyme which cross-links fibrin.

The APTT test has been used to detect disorders of the intrinsic blood coagulation pathway and to monitor patients undergoing anti-coagulation therapy. In the APTT test, an activator compound, a phospholipid and calcium ions are added to the plasma being tested. The time for the plasma to clot is measured from the time the calcium ions are added until the start of coagulation. If there are deficiencies in any of the various factors making up the blood coagulation mechanism, these deficiencies are manifested in abnormal clotting, e.g., failure to clot, excessive prolonged clotting times, or prolonged clot retraction.

There are a number of activators for the APTT test, including silica, kaolin, Ellagic acid and sufatides. See Babson, U.S. Pat. No. 3,880,714 (1975), Speck, U.S. Pat. No. 3,486,981 (1969), and Witt, U.S. Pat. No. 4,672,030 (1987). However, silica and kaolin are heavy particles and tend to "settle" in the test sample during the coagulation assay in the automated instrument. That is, the silica and kaolin will fall out of the solution and the results of the assay may be erroneous.

Use of Ellagic acid-based reagents have given varying results in the APTT test. Ellagic acid has two internal ester bonds which may undergo hydrolysis in an alkaline pH medium. Without being limited by theory, it is thought that the variations in results of the APTT tests using Ellagic acid may be due to a structural change of the Ellagic acid in the reagent.

Sulfatides have been tested by applicants herein, according to the method described in Witt. At 100 ug/ml, the clotting time was 47 seconds, indicating a low level of activity. In addition, sulfatides are approximately 80 times more expensive than the activator of the present invention.

In Japanese patent No. 60-174952 (1985), it is disclosed that orthoquinone compounds coagulated plasma in approximately 5 to 8 minutes. However, the orthoquinone compounds could not be used in an aqueous medium because they are extremely unstable in an aqueous medium. Thus, they must be prepared and used in a water free, organic medium. (See, e.g. Fieser and Fieser, *Organic Chemistry*, 3rd Ed. at p. 716 (D. C. Heath and Company, Boston), and Chem. Ber 37, 4744–4746 at 4746 (1904).) Hence the orthoquinone compounds coagulate only a very small portion of the proteins available in plasma for coagulation. Moreover, the coagulation time disclosed in Japanese patent No. 60-174952 is several minutes longer than that of the present invention. The paraquinone of the present invention thus has a much high level of clotting activity.

SUMMARY OF INVENTION

The present invention is the use of tetrahydroxy-1,4-quinone as an activator component for the activated partial thromboplastin time test of blood coagulation. Tetrahydroxy-1,4-quinone is soluble in aqueous solution and therefore does not settle out of the test sample during assay. Moreover, due to its unique structural character, tetrahydroxy-1,4-quinone provides a homogeneous active species. The experimental data, as particularly reflected in Examples 1–6, suggests that one proton (H) of the four hydroxyl (—OH) groups of the molecule needs to be dissociated, and a metal ion then may bind in the space left by the proton. The dissociation of the proton allows the tetrahydroxy-1,4-quinone to become active for coagulation.

Dissociation of any one of the four hydrogen atoms on the tetrahydroxy-1,4-quinone molecule generates identical ions because the structure of the molecule is symmetrical and all of the four hydroxyl (—OH) groups on the molecule are structurally equivalent. Thus, it is expected that each of the unprotonated molecules from each of the hydroxyl groups should have an identical activity for coagulation. The structural symmetry of the tetrahydroxy-1,4-quinone molecule thus presents an advantage over molecules with no structural symmetry, with unequivalent dissociable protons, or which generate more than one ion species.

DETAILED DESCRIPTION OF THE INVENTION

The disclosed invention involves using 2,3,5,6-tetrahydroxy-1,4-quinone ("THQ") as an activator for the intrinsic blood coagulation pathway. The use of 0.5 to 4.4 mM of THQ in the presence of cupric ($Cu^{2+}$), ferric ($Fe^{3+}$), cobalt ($Co^{2+}$), manganese ($Mn^{2+}$), or nickel ($Ni^{2+}$) ion and phospholipid initiates blood coagulation. The solution of THQ with the added metal ions and phosilipid shall be referred to herein as the "THQ Reagent". The buffer used may be a Glycine-Bicine buffer, or a HEPES (4-(2-hydroxyethyl)-1-piperazineethanesulfonic acid) buffer. In addition, buffers such as sodium bicarbonate and buffers with non-chelating properties, including Tris(hydroxymethy)aminoethane and 4-morpholineethanesulfonic acid, are expected to be suitable buffers.

In testing the clotting or coagulation time, the THQ Reagent is added to the plasma, incubated for 2 minutes at 37° C., and then 25 mM calcium chloride is added. The observed clotting times of the plasma were from about 28 to 48 seconds. The preferred clotting time is in the range of 30 seconds or less. Increased clotting times, such as 40–50 seconds, should be technically as accurate as a clotting time of 30 seconds or less. It is suspected that significantly increased clotting times may result in the loss of sensitivity of the assay.

Incubation of the plasma and the THQ Reagent is required. The best results were obtained with samples incubated for 2 minutes as described in Example 6. However, there was no meaningful difference in the clotting time where the incubation time was extended to 3 minutes. Presently, as supplied by manufacturers, all manual and automated instruments for performing the clotting assay use a temperature of 37° C. Incubation of the samples at room temperature is expected to decrease the rates of the reaction and thereby increase the clotting time.

EXAMPLE 1

Seventy-five point seven milligrams of 2,3,5,6-tetrahydroxy-1,4-quinone hydrate were dissolved in 10 ml of 20 mM sodium hydroxide to prepare a solution of 44 mM THQ. The solution was incubated at room temperature (25° C.) overnight. The solution was then diluted 10-fold with water to make a 4.4 mM solution of THQ. For each ml of the 4.4 mM THQ solution, 0,088 ml of 100 mM $CuCl_2$, 0.042 ml Glycine [$C_2H_5NO_2$] and 0,018 ml of 1 M Bicine [$C_6H_{13}NO_4$] were added.

The solution was then diluted 4-fold with a 21 mM Glycine-8 mM Bicine buffer, pH 7.3. To each ml of the resulting diluted THQ solution, 0,125 ml Cephaline (a rabbit brain extract of Baxter Diagnostics Inc., a phospholipid) was added. The resulting concentrations of THQ and $CuCl_2$ in the THQ Reagent were 0.95 mM, and 1.71 mM, respectively. Three other solutions of THQ Reagents with concentrations of THQ of 0.25 mM, 0.52 mM and 4.4 mM, were prepared similarly.

To test the activity of THQ as an activator for APTT, 0.1 ml of the THQ Reagent was added to 0.1 ml of lyophilized and then reconstituted normal pooled plasma manufactured by Baxter Diagnostics Inc. The resulting mixture was then incubated at 37° C. for 5 minutes, followed by the addition of 0.1 ml of 0.025M $CaCl_2$ solution. The clotting time of the mixture was measured in a Fibrometer or MLA Automatic Coagulation Timer. The results are shown in Table I (n=2). As used throughout this application, "n" represents the number of clotting time determinations made for each assay reported in the tables below.

TABLE I

| CLOTTING TIME OF THQ | |
|---|---|
| THQ CONCENTRATION mM | CLOTTING TIME Seconds |
| 0.25 | 52.3 ± 1.0 |
| 0.52 | 35.7 ± 2.2 |
| 0.95 | 33.8 ± 1.0 |
| 4.40 | 73.6 ± 1.7 |

The 0.95 mM THQ solution showed a higher activity and thus lower clotting time, than the other three samples.

Blank samples which did not contain THQ or $CaCl_2$ did not clot the lyophilized and then reconstituted normal pooled plasma.

Although the specific base to dissolve the THQ hydrate disclosed in this example is NaOH, it is expected that 2,3,5,6-THQ hydrate is soluble in any base solution in which one or more protons of the THQ hydrate can be dissociated. Moreover, it is expected that the THQ will perform as an activator with other concentrations of glycine and bicine. The best ratio has been disclosed in Example 1.

EXAMPLE 2

A solution with a higher concentration of THQ was prepared and tested. The concentration of THQ in the buffered-Cephaline treated mixture of Example 1 was increased to 2.6 mM. The incubation time of the mixture of the THQ Reagent and (reconstituted) lyophilized normal pooled plasma was 2 minutes. The remaining experimental conditions were those described in Example 1.

The clotting time observed was 31.3±1.7 seconds (n=6).

EXAMPLE 3

The effect of the concentration of $CuCl_2$ was studied. The concentration of the $CuCl_2$ solution was varied, while the rest of the solution concentrations of Example 1 were not changed. The incubation time at 37° C. of the THQ Reagent, plasma, and $CuCl_2$ mixture was 2 minutes. The clotting time was measured as described in Example 1. The results are shown in Table II (n=2).

TABLE II

| THE EFFECT OF CUPRIC CHLORIDE CONCENTRATION | |
|---|---|
| $CuCl_2$ CONCENTRATION mM | CLOTTING TIME Seconds |
| 0.9 | 37.6 ± 0.2 |
| 1.4 | 33.9 ± 0.1 |
| 1.7 | 33.8 ± 1.0 |
| 2.3 | 42.4 ± 2.0 |

The data indicate that the optimum concentration of $CuCl_2$ in these given experimental conditions was between about 1.4 to 1.7 mM.

EXAMPLE 4

The effect of other metal compounds at a concentration of 1.7 mM in a mixture of concentration of 1.1 mM THQ and lyophilized normal plasma was studied. (It is suspected that there were traces of metal ions present in other chemical reagents used. However, such trace amounts were not sufficient to activate the THQ.) The remaining experimental conditions were those as described in Example 1.

TABLE III

EFFECT OF METAL COMPOUNDS

| COMPOUNDS 1.7 mM | CLOTTING TIME Seconds | n |
|---|---|---|
| $CuCl_2$ | 34.5 ± 3.1 | 2 |
| $Co(C_2H_3O_2)_2$ | 38.7 ± 8.4 | 5 |
| $FeCl_3$ | 46.6 ± 2.8 | 2 |
| $MnSO_4$ | 47.4 ± 0.4 | 2 |
| $NiCl_2$ | 64.1 ± 0.8 | 2 |

Among the five metal compounds tested, cupric chloride and cobalt acetate in THQ Reagent showed the highest clotting activity.

EXAMPLE 5

The importance of a metal ion with THQ as an activator for the clotting process was studied by including a chelating compound in the assay. A chelating compound is one which binds with metal ions, thus decreasing their availability to participate in the clotting process. Histidine is an amino acid, like Glycine, but has a chelating property. (See, e.g., R. B. Martin, *Introduction to Biophysical Chemistry*, McGraw-Hill, New York, p. 337, 1964.) The Glycine in Example 3 was replaced by Histidine. The cupric chloride concentration used was 1.4 mM. The remaining experimental conditions were those as described in Example 1. In the absence of added metal ion, the clotting time was over 100 seconds, or no clot was observed. The elevated clotting time indicates the importance of metal ion in the clotting process.

EXAMPLE 6

The Glycine-Bicine buffer of Example 1 was replaced by HEPES, (4-(2-hydroxyethyl)-1-piperazineethanesulfonic acid) and the THQ concentration was increased to 2.72 mM. The incubation time at 37° C. for the mixture of "THQ Reagent and (reconstituted) lyophilized normal pooled plasma was 2 minutes. A solution of 0.02M calcium chloride was added. " The results are shown in Table IV (n=4). The lyophilized normal pooled plasma was described in Example 1.

TABLE IV

THE CLOTTING ACTIVITY OF THQ IN HEPES BUFFER

| HEPES mM | pH | METAL COMPOUNDS 1.71 mM | CLOTTING TIME Seconds |
|---|---|---|---|
| 20 | 8.0 | $CuCl_2$ | 27.8 ± 0.2 |
| 50 | 8.0 | $CuCl_2$ | 28.9 ± 0.7 |
| 50 | 7.5 | $ZnCl_2$ | 27.9 ± 1.3 |

In addition, the clotting time was measured (n=2) using 50 mM HEPES, with a pH of approximately 7.0, with a concentration of $CuCl_2$ of 1.71 mM, THQ Reagent of 2.72 mM and otherwise under the same reaction conditions as Example 6. The clotting time was 25.4 seconds. The concentration of 2.72 mM THQ Reagent was found to work the best where the HEPES buffer was substituted for the Glycine-Bicine buffer of Example 1. Lesser concentrations of the THQ Reagent are also expected to provide acceptable clotting times.

EXAMPLE 7

A THQ Reagent was used to study the usefulness of the reagent for the detection of coagulation disorders.

The addition of the THQ Reagent as described in Example 1 to Factor XII deficient plasma (instead of lyophilized normal plasma), in buffer solutions described in Example 1 and under the same incubation conditions described in Example 1, with the addition of calcium chloride, did not activate the coagulation pathway plasma. Because Factor XII is the first coagulation factor in the intrinsic coagulation pathway, the data suggests that Factor XII may be responsible for interaction with THQ. Similarly, plasma samples deficient of Factor VIII or IX (Hemophilia Type A or Type B Plasma Samples) mixed with a THQ Reagent did not clot using the reaction conditions and reagents of Example 1 (except substituting the deficient plasma samples for the normal pooled plasma of Example 1). This data suggests that the deficiency or absence of Factor VIII or IX can be detected by the use of THQ as the activator. These results indicate the usefulness of the THQ reagent for the detection of coagulation disorders.

EXAMPLE 8

A structural analog of THQ, Rhodizonic Acid disodium salt (5,6-dihydroxy-5-cyclohexene-1,2,3,4-tetrone dihydrate disodium salt) was dissolved in 20 mM sodium hydroxide. Buffer ions and cupric chloride of the same concentrations as described in Example 1 were added to the Rhodizonic Acid solution, and tested using the same procedure described as in Example 1. The clotting time observed with 2.2 mM Rhodizonic Acid solution was 45.1±1.8 seconds (n=2). This result indicates a low-level of activity.

Paraquinones of the mono-, di- and tri- hydroxy species and their derivatives are expected to produce similar results. In addtion, dimers and multimers of these compounds as well as dimers and multimers of THQ may also be potent activators for coagulation. THQ, its derivatives and its analogs may be conjugated to R groups such as alkyl groups or substituted alkyl groups which include proteins and may also be conjugated to large particles and used as activators for APTT. In general, the reaction rate for such compounds on a solid surface is faster than that in aqueous solution. Metaquinones are not known to exist.

While the examples given herein have used human plasma, the APTT activators of the present invention may also be appropriate activators in the clotting process of other species' blood.

We claim:

1. A method for activation of the intrinsic coagulation pathway comprising the steps of:
   a) Preparing an aqueous solution of a compound with the structure;

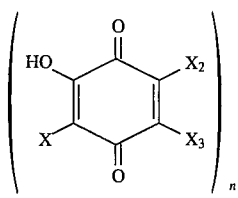

wherein X is selected from the group consisting of H, OH, and OR, wherein R is an alkyl group, wherein $X_2$ is selected from the group consisting of H, OH, and OR, wherein R is an alkyl group, and wherein $X_3$ is selected from the group consisting of H, OH, and OR, wherein R is an alkyl group and where n=at least 1;

b) Buffering the aqueous solution of step a) so that the aqueous solution has a pH greater than 7.0;

c) Adding an aqueous solution including metal ions selected from the group consisting of cupric, cobalt, ferric, and manganese to the aqueous solution resulting from step b);

d) Adding a phospholipid to the solution resulting from step c);

e) Adding plasma to the solution formed as a result of step d);

f) Incubating the mixture resulting from step e); and g) Adding an aqueous solution of calcium chloride to the incubated mixture resulting from step f) resulting in the formation of clot in approximately 30 to 50 seconds.

2. The method of claim 1 wherein: the buffer of step b) is selected from the group consisting of Glycine-Bicine, of a pH of approximately 7.0 to 7.3 and HEPES of a pH of approximately 7.0 to 8.0; the metal ions of step c) are selected from the group consisting of cupric, cobalt, ferric, zinc and manganese; the resulting concentration of the compound of step a) is between approximately 0.50 mM and 2.75 mM, and the resulting metal ion concentration is between approximately 0.90 mM and 2.30 mM after step d); and the incubation time and temperature of step f) is at least about two minutes and less than about three and one half minutes at about 37° C.

3. The method of claim 1 wherein the buffer of step b) is HEPES of a pH of approximately 7.0 to 8.0; the metal ions of step c) are selected from the group consisting of cupric, cobalt, ferric, zinc, manganese; the resulting concentration of the compound of step a) is approximately 2.75 mM and the resulting metal ion concentration is between approximately 0.9 mM and 2.5 mM after step d); and the incubation time and temperature of step f) is at east about two minutes and less than about three and one half minutes at about 37° C.

4. The method of claim 2 wherein the compound of step a) is a compound having the structure

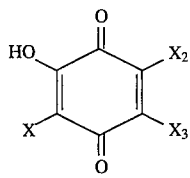

wherein X is selected from the group consisting of H and OH; wherein $X_2$ is selected from the group consisting of H and OH; where $X_3$ is selected from the group consisting of H and OH.

5. The method of claim 3 wherein the compound of step a) is a compound having the structure

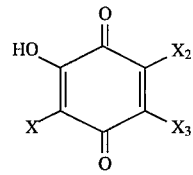

wherein X is selected from the group consisting of H and OH; wherein $X_2$ is selected from the group consisting of H and OH; and wherein $X_3$ is selected from the group consisting of H and OH.

6. A method for detection of clotting disorders of the intrinsic coagulation pathway comprising the steps of:

a) Preparing an aqueous solution of a compound with the structure:

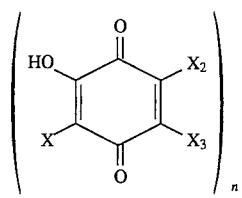

wherein X is selected from the group consisting of H, OH, and OR, wherein R is an alkyl group, wherein $X_2$ is selected from the group consisting of H, OH, and OR, wherein R is an alkyl group, and wherein $X_3$ is selected from the group consisting of H, OH, and OR, wherein R is an alkyl group, and where n=at least 1;

b) Buffering the aqueous solution of step a) so that the aqueous solution has a pH greater than 7.0;

c) Adding an aqueous solution including metal ions selected from the group consisting of cupric, cobalt, ferric, and manganese to the aqueous solution resulting from step b);

d) Adding a phospholipid to the solution resulting from step c);

e) Adding plasma to the solution formed as a result of step d);

f) Incubating the mixture resulting from step e); and g) Adding an aqueous solution of calcium chloride to the incubated mixture resulting from step f); and h) Observing the result of step g) to determine whether and when a clot is formed.

7. The method of claim 6 wherein the buffer of step b) is selected from the group consisting of Glycine-Bicine, of a pH of approximately 7.0 to 7.3 and HEPES of a pH of approximately 7.0 to 8.0; the metal ions of step c) are selected from the group consisting of cupric, cobalt, ferric, and manganese; the resulting concentration of the compound of step a) is between approximately 0.50 mM and 2.75 mM, and the resulting metal ion concentration is between approximately 0.90 mM and 2.30 mM after step d); and the incubation time and temperature of step f) is at least about two minutes and less than about three and one half minutes at about 37° C.

8. The method of claim 6 wherein the buffer of step b) comprises HEPES of a pH of approximately 7.0 to 8.0; the metal ions of step c) are selected from the group consisting of cupric, cobalt, ferric, and manganese; the resulting concentration of the compound of step a) is between approximately 0.50 mM and 2.75 mM, and the resulting metal ion concentration is between approximately 0.90 mM and 2.30 mM after step d); and the incubation time and temperature of step f) is at least about two minutes and less than about three and one half minutes at about 37° C.

9. The method of claim 7 wherein the compound of step a) is a compound having the structure

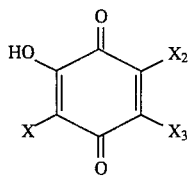

wherein X is selected from the group consisting of H and OH; wherein $X_2$ is selected from the group consisting of H and OH; and wherein $X_3$ is selected from the group consisting of H and OH.

10. The method of claim 8 wherein the compound of step a) is a compound having the structure

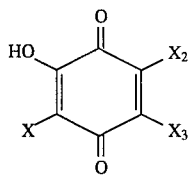

wherein X is selected from the group consisting of H and OH; wherein $X_2$ is selected from the group consisting of H and OH; and wherein $X_3$ is selected from the group consisting of H and OH.

11. An activated partial thromboplastin time test reagent comprising a phospholipid and a compound with the structure:

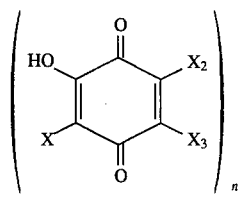

wherein X is selected from the group consisting of H, OH, and OR, wherein R is alkyl group, wherein $X_2$ is selected from the group consisting of H, OH, and OR, wherein R is an alkyl group, and wherein $X_3$ is selected from the group consisting of H, OH, and OR, wherein R is an alkyl group and where n=at least 1, as the chemical activator wherein the time for the clot to begin to form is between about 30 to 50 seconds.

12. The activated partial thromboplastin time test reagent of claim 11 wherein the chemical activator compound is and a compound having the structure

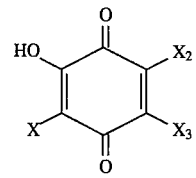

wherein X is selected from the group consisting of H and OH;

wherein $X_2$ is selected from the group consisting of H and OH; and wherein $X_3$ is selected from the group consisting of H and OH.

13. The activated partial thromboplastin time test reagent of claim 12 wherein the concentration of the chemical activator compound is between approximately 0.50 mM and 2.75 mM.

14. The activated partial thromboplastin time test reagent of claim 12, further comprising:
    a) a buffer of selected from the group consisting of Glycine-Bicine, of a pH of approximately 7.0 to 7.3 and HEPES of a pH of approximately 7.0 to 8.0;
    b) metal ions selected from the group consisting of cupric, cobalt, ferric, and manganese;
    c) calcium chloride;
    wherein the concentration of said chemical activator is between approximately 0.50 mM and 2.75 mM, and the metal ion concentration is between approximately 0.90 mM and 2.30 mM;
    and wherein said activator compound, buffer, metal ions and phospholipid are incubated for at least about two minutes and less than about three and one half minutes at about 37° C. prior to the addition of the calcium chloride.

15. The activated partial thromboplastin time test reagent of claim 14 wherein the buffer of step b) is HEPES of a pH of approximately 7.0 to 8.0.

* * * * *